United States Patent
Bisgaier et al.

(10) Patent No.: US 8,557,835 B2
(45) Date of Patent: Oct. 15, 2013

(54) STATIN-CARBOXYALKYLETHER COMBINATIONS

(75) Inventors: Charles Larry Bisgaier, Ann Arbor, MI (US); Roger Schofield Newton, Ann Arbor, MI (US)

(73) Assignee: Warner-Lambert Company, LLC, New York, NY (US)

( * ) Notice: Subject to any disclaimer, the term of this patent is extended or adjusted under 35 U.S.C. 154(b) by 620 days.

(21) Appl. No.: 11/961,032

(22) Filed: Dec. 20, 2007

(65) Prior Publication Data

US 2009/0118317 A1 May 7, 2009

Related U.S. Application Data

(63) Continuation of application No. 11/067,847, filed on Feb. 28, 2005, now abandoned, which is a continuation of application No. 10/938,203, filed on Sep. 10, 2004, now Pat. No. 7,141,608, which is a continuation of application No. 10/245,005, filed on Sep. 17, 2002, now abandoned, and a continuation of application No. 10/018,617, filed as application No. PCT/IB01/00026 on Jan. 11, 2001, now Pat. No. 6,861,555, said application No. 10/245,005 is a continuation of application No. 10/040,195, filed on Oct. 24, 2001, now abandoned, which is a continuation of application No. 09/485,241, filed as application No. PCT/US98/24679 on Nov. 20, 1998, now abandoned.

(60) Provisional application No. 60/177,823, filed on Jan. 25, 2000, provisional application No. 60/069,375, filed on Dec. 12, 1997.

(51) Int. Cl.
*A61K 31/40* (2006.01)
*A61K 31/435* (2006.01)
*A61K 31/351* (2006.01)
*A61K 31/21* (2006.01)

(52) U.S. Cl.
USPC ............ 514/277; 514/423; 514/460; 514/510

(58) Field of Classification Search
None
See application file for complete search history.

(56) References Cited

U.S. PATENT DOCUMENTS

| | | | | |
|---|---|---|---|---|
| 5,298,627 A | 3/1994 | Butler et al. | ............ | 548/517 |
| 5,648,387 A | 7/1997 | Bisgaier et al. | ............ | 514/547 |

FOREIGN PATENT DOCUMENTS

| | | | | |
|---|---|---|---|---|
| EP | 0455042 | 6/1991 | ............ | A61K 31/19 |
| EP | 0753298 | 1/1997 | ............ | A61K 31/425 |
| WO | WO 9630328 | 2/1996 | ............ | C07C 59/305 |
| WO | WO 9716187 | 5/1997 | ............ | A61K 31/415 |
| WO | WO 9930704 | 6/1999 | | |

OTHER PUBLICATIONS

Goodman & Gilman's, The pharmacological basis of thereapeutics, 9th Edition, 1995, pp. 56-58.
Heinonen, et al., Atorvastatin, a New HMG-CoA reductase inhibitor as monotherapy and combined with colestipol. *Journal of Cardiovascular Pharmacology and Therapeutics* 1996, pp. 117-122. vol. 1(2).
Illingworth, et al., Influence of Lovastatin Plus Gemfibrozli on Plasma Lipids and Lipoproteins in Patients with Hetepzyous Familial Hypercholesterolemia, *Circulation*, 1989, pp. 590=596, vol. 79 (3).
Mandema, et al., Model-based development of gemcabene, a new lipid-altering agent. *The AAPS Journal* 2005, pp. E513-E522 vol. 7(3).
Merck Index, 12th Edition, p. THER-10, 1996.
Pauciullo, et al., Efficacy and safety of a combination of fluvastatin and bezafilbrate in patients with mixed hyperlipdaema, *Atheroscierosis*, 2000, pp. 429-436, vol. 150.
PCT International Search Report, PCT/IB01/00026.
PCT International Search Report, PCT/US98/24679.
Rubins, et al., Gemfibrozil for the secondary prevention of coronary heart disease in men with low levels of high-density lipoprotein cholesterol. *New England Journal of Medicine*, 1999, pp. 410-418, vol. 341(6).
Tikkamen, et al., Abstract, *Current Opinion in Lipidology*, 1996,pp. 385-388, vol. 7 (6).
Cone, C. et al., "Demographic Determinants of Response to Statin Medications", Am J Healt-Syst Pharm, vol. 68, 2001, pp. 511-517.
Fox, K. M. et al., "Effectiveness of Statins in Medicare-Eligible Patients and Patients < 65 Years Using Clinical Practice Data", Int J Clinc Pract, vol. 61, No. 10, 2007, pp. 1634-1642.
Jacobson, T. A., "The Safety of Aggressive Statin Therapy: How Much Can Low-Density Lipoprotein Cholesterol Be Lowered?", Mayo Clinic Proceedings, vol. 81, No. 9, 2006, pp. 1225-1231.
Jones, P. H., "Fenofibric Acid Plus Statin Combination Therapy for the Treatment of Mixed Dyslipidemia", Clin. Lipidol., vol. 4, No. 6, 2009, pp. 699-711.
Josan, K et al., "The Efficacy and Safety of Intensive Statin Therapy: A Meta-Analysis of Randomized Trails", CMAJ, vol. 178, No. 5, 2008, pp. 576-584.
Marais, A. D. et al., "Statins in Homozygous Familial Hypercholesterolemia", Current Atherosclerosis Reports, vol. 4, 2002, pp. 19-25.
Martineau, P. et. al., "Effect of Individualizing Starting Doses of a Statin According to Baseline LDL-Cholesterol Levels on Achieving Cholesterol Targets: The Achieve Cholesterol Targets Fast With Atorvastatin Stratified Titration (ACTFAST) Study", Atherosclerosis, vol. 191, 2007, pp. 135-146.
McKenney, J. M., "Optimizing LDL-C Lowering With Statins", Am J Ther, vol. 11, 2004, pp. 54-59.

(Continued)

*Primary Examiner* — Layla Bland
*Assistant Examiner* — Bahar Craigo
(74) *Attorney, Agent, or Firm* — Honigman Miller Schwartz and Cohn; Cynthia Marie Bott; Jonathan P. O'Brien

(57) ABSTRACT

The invention is a pharmaceutical composition comprising a carboxyalkylether which lowers triglycerides and elevated HDL, and a statin which inhibits HMG-CoA reductase, thereby reducing LDL, said composition being useful for treating vascular diseases.

11 Claims, No Drawings

(56) References Cited

OTHER PUBLICATIONS

Stein, E., "Results of Phase I/II Clinical Trials With Ezetimibe, a Novel Selective Cholesterol Absorption Inhibitor", European Heart Journal Supplements, vol. 3, Suppl. E, 2001, pp. E11-E16.
Vandenberg, B. F. et. al., "Management of the Patient With Statin Intolerance", Curr Atheroscler Rep, vol. 12, 2010, pp. 48-57.
Vasudevan, A. R. et. al., "Effective Use of Combination Lipid Therapy", Current Cardiology Reports, vol. 7, 2005, pp. 471-479.
Weng, T. C. et. al., "A Systematic Review and Meta-Analysis on the Therapeutic Equivalence of Statins", J Clin Pharm Ther, vol. 35, 2010, pp. 139-151.

STATIN-CARBOXYALKYLETHER COMBINATIONS

FIELD OF THE INVENTION

This invention concerns a combination of a statin compound, which is known to cause a reduction in plasma levels of low-density lipoprotein (LDL) cholesterol, and a carboxyalkylether, a compound which causes a rise in high-density lipoprotein (HDL) cholesterol. The combination is useful for treating vascular disorders and diabetes mellitus.

BACKGROUND OF THE INVENTION

Several clinical studies have established that lowering certain forms of cholesterol in a mammal is an effective way to treat and prevent heart attacks, sudden death, and angina, both in subjects having higher than normal levels of circulating cholesterol, as well as those having normal levels of cholesterol. Lowering LDL, the bad form of cholesterol, is now one of the primary objectives of physicians treating patients who have, or who have a high risk of developing, cardiovascular diseases such as coronary heart disease, atherosclerosis, myocardial infarction, stroke, cerebral infarction, and even restenosis following balloon angioplasty. Many physicians are now utilizing cholesterol lowering agents purely as a prophylactic treatment in healthy subjects whose cholesterol levels are normal, thereby guarding against development of cardiovascular diseases.

The most commonly used cholesterol lowering agents are the statins, which are compounds which inhibit the enzyme 3-hydroxy-3-methylglutaryl-coenzyme A (HMG-CoA) reductase, the enzyme responsible for catalyzing the conversion of HMG-CoA to mevalonate, which is an early and rate-limiting step in the cholesterol biosynthetic pathway.

There are several forms of circulating blood cholesterol which occur naturally in mammals. Some forms are considered "bad" cholesterol, while other forms are considered "good" cholesterol and are essential for good health. The good form of cholesterol has been established to be HDL. A bad cholesterol is LDL. Another form of LDL cholesterol, the primary bad form, is a modified form of LDL called lipoprotein(a), or "Lp(a)". High levels of Lp(a) are now believed to be detrimental and can lead to cardiovascular diseases, and is one of the major risk factors leading to death from heart disease.

Because vascular diseases such as coronary heart disease, stroke, and even peripheral vascular disease, remain a leading cause of death and disability throughout the world, the need continues to develop new and improved treatments, as well as agents that will actually prevent the formation of these diseases.

We have now discovered that treatment and prevention of vascular diseases can be effected by administering a combination of a statin with a carboxyalkylether. Typical carboxyalkylethers are described in U.S. Pat. No. 5,648,387 incorporated herein by reference.

SUMMARY OF THE INVENTION

This invention provides a pharmaceutical composition comprised of an effective amount of a statin and an effective amount of a carboxyalkylether. More particularly, the invention is a combination of a statin with a carboxyalkylether having Formula I

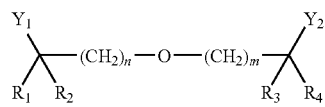

wherein
n and m independently are integers from 2 to 9;
$R_1$, $R_2$, $R_3$, and $R_4$ independently are $C_1$-$C_6$ alkyl, $C_1$-$C_6$ alkenyl, $C_2$-$C_6$ alkynyl, and $R_1$ and $R_2$ together with the carbon to which they are attached, and $R_3$ and $R_3$ together with the carbon to which they are attached, can complete a carbocyclic ring having from 3 to 6 carbons;
$Y_1$ and $Y_2$ independently are COOH, CHO, tetrazole, and COOR$_5$ where $R_5$ is $C_1$-$C_6$ alkyl, $C_2$-$C_6$ alkenyl, $C_2$-$C_6$ alkynyl; and
where the alkyl, alkenyl, and alkynyl groups may be substituted with one or two groups selected from halo, hydroxy, $C_1$-$C_6$ alkoxy, and phenyl.

Preferred compounds to be employed in this invention have the above formula wherein n and m are the same integer, and wherein $R_1$, $R_2$, $R_3$, and $R_4$ each are alkyl.

Further preferred are compounds wherein $Y_1$ and $Y_2$ independently are COOH or COOR$_5$ where $R_5$ is alkyl.

The most preferred compounds to be employed have the Formula II

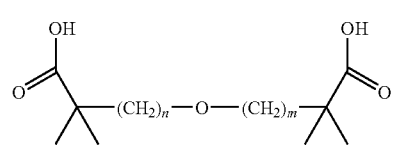

wherein n and m are each an integer selected from 2, 3, 4, or 5, ideally 4 or 5.

An especially preferred compound has the Formula III

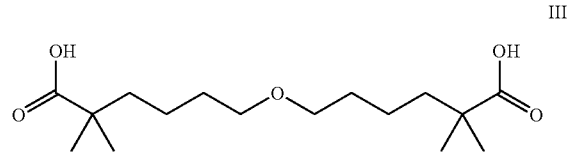 [SMILES: CC(C)(CCCCOCCCCC(C)(C)C(=O)O)C(=O)O]

The combinations of this invention can also employ the pharmaceutically acceptable salts of the acids of Formula I.

Typical statins to be employed in combination with the compound of Formula I include atorvastatin, simvastatin, pravastatin, cerivastatin, mevastatin, velostatin, fluvastatin, lovastatin, dalvastatin, and fluindostatin. The statins can be employed as pharmaceutically acceptable salts.

A particularly preferred composition of this invention utilizes a carboxyalkylether of Formula II together with a statin selected from atorvastatin calcium, pravastatin sodium, simvastatin, lovastatin, and cerivastatin. The most preferred composition employs the compound of Formula III with atorvastatin calcium.

Also provided by the invention are methods for treating vascular diseases such as peripheral vascular disease, coronary heart disease, stroke, and restenosis. The invention provides a method for lowering Lp(a), plasma triglycerides, very low-density lipoprotein (VLDL) cholesterol, LDL cholesterol, and apolipoprotein B. The invention additionally provides a method for elevating plasma HDL cholesterol, apolipoprotein A-I, and apolipoprotein E. The invention also provides a method for treating and preventing noninsulin-dependent diabetes mellitus by increasing insulin sensitivity by administering a combination of this invention.

DETAILED DESCRIPTION OF THE INVENTION

We have discovered that combining a statin with a carboxyalkylether provides a surprisingly effective composition for treating and preventing vascular diseases, as well as diabetes mellitus. As noted above, the "carboxyalkylethers" as used herein are compounds such as those described in U.S. Pat. No. 5,648,387 incorporated herein by reference. The compounds can be the free acid, a salt form, or the tetrazolyl or aldehyde analog.

The other active component of the combinations of this invention is a statin. The term "statin", where used in the specification and the appendant claims, is synonymous with the terms "3-hydroxy-3-methylglutaryl-Coenzyme A reductase inhibitor" and "HMG-CoA reductase inhibitor." These three terms are used interchangeably throughout the specification and appendant claims. As the synonyms suggest, statins are inhibitors of 3-hydroxy-3-methylglutaryl-Coenzyme A reductase and, as such, are effective in lowering the level of blood plasma cholesterol. Statins and pharmaceutically acceptable salts thereof are particularly useful in lowering low-density lipoprotein cholesterol (LDL-C) levels in mammals and particularly in humans.

The HMG-CoA reductase inhibitors suitable for use herein include, but are not limited to, simvastatin, pravastatin, rivastatin, mevastatin, fluindostatin, cerivastatin, velostatin, fluvastatin, dalvastatin, dihydrocompactin, compactin, or lovastatin; or a pharmaceutically acceptable salt of simvastatin, pravastatin, rivastatin, cerivastatin, mevastatin, fluindostatin, velostatin, fluvastatin, dalvastatin, dihydrocompactin, compactin, lovastatin, or pharmaceutically acceptable salts thereof. However, it is to be noted that atorvastatin calcium is a particularly preferred statin to be employed in the present combination. See U.S. Pat. No. 5,273,995 incorporated herein by reference.

The statins disclosed herein are prepared by methods well-known to those skilled in the art. Specifically, simvastatin may be prepared according to the method disclosed in U.S. Pat. No. 4,444,784, which is incorporated herein by reference. Pravastatin may be prepared according to the method disclosed in U.S. Pat. No. 4,346,227, which is incorporated herein by reference. Cerivastatin may be prepared according to the method disclosed in U.S. Pat. No. 5,502,199, which is incorporated herein by reference. Cerivastatin may alternatively be prepared according to the method disclosed in European Patent Application Publication No. EP617019. Mevastatin may be prepared according to the method disclosed in U.S. Pat. No. 3,983,140, which is incorporated herein by reference. Velostatin may be prepared according to the methods disclosed in U.S. Pat. No. 4,448,784 and U.S. Pat. No. 4,450,171, both of which are incorporated herein by reference. Fluvastatin may be prepared according to the method disclosed in U.S. Pat. No. 4,739,073, which is incorporated herein by reference. Compactin may be prepared according to the method disclosed in U.S. Pat. No. 4,804,770, which is incorporated herein by reference. Lovastatin may be prepared according to the method disclosed in U.S. Pat. No. 4,231,938, which is incorporated herein by reference. Dalvastatin may be prepared according to the method disclosed in European Patent Application Publication No. 738510 A2. Fluindostatin may be prepared according to the method disclosed in European Patent Application Publication No. 363934 A1. Dihydrocompactin may be prepared according to the method disclosed in U.S. Pat. No. 4,450,171, which is incorporated herein by reference.

It will be recognized that certain of the above statins contain either a free carboxylic acid or a free amine group as part of the chemical structure. Further, certain statins within the scope of this invention contain lactone moieties, which exist in equilibrium with the free carboxylic acid form. These lactones can be maintained as carboxylates by preparing pharmaceutically acceptable salts of the lactone. Thus, this invention includes pharmaceutically acceptable salts of those carboxylic acids or amine groups. The expression "pharmaceutically acceptable salts" includes both pharmaceutically acceptable acid addition salts and pharmaceutically acceptable cationic salts. The expression "pharmaceutically acceptable cationic salts" is intended to define but is not limited to such salts as the alkali metal salts, (e.g., sodium and potassium), alkaline earth metal salts (e.g., calcium and magnesium), aluminum salts, ammonium salts, and salts with organic amines such as benzathine (N,N'-dibenzylethylenediamine), choline, diethanolamine, ethylenediamine, meglumine (N-methylglucamine), benethamine (N-benzylphenethylamine), diethylamine, piperazine, tromethamine (2-amino-2-hydroxymethyl-1,3-propanediol) and procaine. The expression "pharmaceutically acceptable add addition salts" is intended to define but is not limited to such salts as the hydrochloride, hydrobromide, sulfate, hydrogen sulfate, phosphate, hydrogen phosphate, dihydrogenphosphate, acetate, succinate, citrate, methanesulfonate (mesylate) and p-toluenesulfonate (tosylate) salts.

The pharmaceutically acceptable cationic salts of statins containing free carboxylic acids may be readily prepared by reacting the free acid form of the statin with an appropriate base, usually one equivalent, in a co-solvent. Typical bases are sodium hydroxide, sodium methoxide, sodium ethoxide, sodium hydride, potassium methoxide, magnesium hydroxide, calcium hydroxide, benzathine, choline, diethanolamine, piperazine, and tromethamine. The salt is isolated by concentration to dryness or by addition of a non-solvent. In many cases, salts are preferably prepared by mixing a solution of the acid with a solution of a different salt of the cation (sodium or potassium ethylhexanoate, magnesium oleate), employing a solvent (e.g., ethyl acetate) from which the desired cationic salt precipitates, or can be otherwise isolated by concentration and/or addition of a non-solvent.

The pharmaceutically acceptable acid addition salts of statins containing free amine groups may be readily prepared by reacting the free base form of the statin with the appropriate acid. When the salt is of a monobasic acid (e.g., the hydrochloride, the hydrobromide, the p-toluenesulfonate, the acetate), the hydrogen form of a dibasic acid (e.g., the hydrogen sulfate, the succinate), or the dihydrogen form of a tribasic acid (e.g., the dihydrogen phosphate, the citrate), at least one molar equivalent and usually a molar excess of the acid is employed. However, when such salts as the sulfate, the hemisuccinate, the hydrogen phosphate, or the phosphate are desired, the appropriate and exact chemical equivalents of acid will generally be used. The free base and the acid are usually combined in a co-solvent from which the desired salt precipitates, or can be otherwise isolated by concentration and/or addition of a non-solvent.

In addition, the carboxyalkylethers and pharmaceutically acceptable acid addition salts thereof may occur as hydrates or solvates. Further, the statins of the instant invention and the pharmaceutically acceptable salts of the statins of the instant invention may also occur as hydrates or solvates. Said hydrates and solvates are also within the scope of the invention.

The pharmaceutical combinations and methods of this invention are all adapted to therapeutic use as agents in the prevention and treatment of atherosclerosis, angina pectoris, and a condition characterized by the presence of both hypertension and hyperlipidemia in mammals, particularly humans. Further, since these diseases and conditions are closely related to the development of cardiac disease and adverse cardiac conditions, these combinations and methods, by virtue of their action as antiatherosclerotics, antianginals, antihypertensives, and antihyperlipidemics are useful in the management of cardiac risk in subjects at risk of developing adverse cardiac conditions and in subjects at risk of suffering adverse cardiac events.

The utility of the compositions of the present invention as medical agents in the treatment of atherosclerosis in mammals (e.g., humans) is demonstrated by the activity of the compounds of this invention in conventional assays and in a clinical protocol such as those described below.

Example 1

The metabolic effects of atorvastatin calcium (CI-981) and the compound of Formula III (CI-1027), alone and in combination, were evaluated in rats according to the following protocol.

Male Sprague-Dawley rats weighing from 201 to 225 grams were purchased from Charles Rivers Laboratories. The animals were fed a high cholesterol chow diet (Ralston Purina Chow 150), and given water ad libitum. Atorvastatin calcium (CI-981 at 30 mg/kg) and 6,6'-oxybis-(2,2-dimethylhexanoic acid calcium salt (CI-1027 at 30 mg/kg) were suspended individually, and the combination of 30 mg/kg of CI-981 plus 10 mg/kg of CI-1027 was suspended, in a mixture of 1.5% carboxymethylcellulose (sodium salt, low viscosity, Sigma item C-8758, St. Louis, Mo.) plus 0.2% Tween-20 (Sigma item P-1379, St. Louis, Mo.). The suspensions were administered by oral gavage to each test animal (each dose regimen was given to 8 [N=8] test animals) between 6:00 and 9:00 AM each day for 14 days. A group of control animals (N=8) received the vehicle alone. After 14 days of treatment blood samples were drawn, and plasma levels of lipid and lipoprotein were determined. The results are presented below in Table 1.

TABLE 1

Effects of Two Weeks of Treatment With CI-981, CI-1027, and Combination CI-981 + CI-1027 in Chow Fed Rats

| Treatment Group | mg/kg/day | N | Triglycerides (mg/dL) | Total Cholesterol (mg/dL) | VLDL (mg/dL) | LDL (mg/dL) | HDL (mg/dL) | HDL VLDL + LDL |
|---|---|---|---|---|---|---|---|---|
| Control | | 8 | 118 ± 11 | 41 ± 1 | 6.1 ± 0.6 | 11.3 ± 0.8 | 23 ± 1 | 1.37 ± 0.10 |
| CI-981 | 30 | 8 | 87 ± 11 | 49 ± 3 | 7.9 ± 1.0 | 19.1 ± 1.6 | 22 ± 2 | 0.86 ± 0.11 |
| CI-1027 | 10 | 8 | 58 ± 9 | 58 ± 4 | 3.2 ± 0.6 | 3.4 ± 0.4 | 52 ± 4 | 8.57 ± 0.99 |
| CI-981 + CI-1027 | 30/10 | 8 | 63 ± 8 | 49 ± 2 | 5.6 ± 1.0 | 11.1 ± 1.7 | 33 ± 2 | 2.59 ± 0.62 |

Table 2 below shows the percentage (%) change in the treatment groups compared to the control group.

TABLE 2

Percentage Change From Controls Caused by CI-981, CI-1027, and Combination CI-981 + CI-1027 in Chow Fed Rats

| Control | mg/kg/day | N | Triglycerides (% change) | Total Cholesterol | VLDL | LDL | HDL | HDL VLDL + LDL |
|---|---|---|---|---|---|---|---|---|
| | | 8 | 0 | 0 | 0 | 0 | 0 | 0 |
| CI-981 | 30 | 8 | −26 | +19 | +30 | +69 | −4 | −37 |
| CI-1027 | 10 | 8 | −51 | +42 | −48 | −70 | +126 | +526 |
| CI-981 + CI-1027 | 30/10 | 8 | −47 | +19 | −8 | −2 | +43 | +89 |

Example 2

The above experiment was repeated using genetically altered mice, namely LDL receptor knockout mice. LDLr(-\-) mice were obtained from Jackson Laboratories. A colony was established and maintained. Female mice were selected for the experiment, and were maintained on a normal chow diet (Ralston Purina), and water was available ad libitum. The mice were housed 2 to 4 per cage in temperature controlled (24° C.) rooms on a 12-hour light/12-hour dark cycle (lights were turned on at 6:00 AM daily), prior to and during the experiment. The test compounds were formulated as suspensions in the same vehicle as described in Example 1 (1.5% carboxymethyl-cellulose plus 0.2% Tween-20). Both CI-981 and CI-1027 were formulated for individual doses of 30 and 60 mg/kg. The combination of CI-981+CI-1027 was formulated for doses of 30 mg/kg CI-981+30 mg/kg CI-1027, and 60 mg/kg CI-981+60 mg/kg CI-1027. A group of 10 animals (N=10) were used as controls, and received vehicle alone. One group of 10 mice received CI-981 alone; a second group of 10 mice received CI-1027 alone; a third group of 10 mice received the combination of CI-981+CI-1027 (30 mg/kg+30 mg/kg); and the fourth group of 10 mice received the combination of CI-981+CI-1027 (60 mg/kg+60 mg/kg). The animals received doses of test compounds by oral gavage between 6:00 and 9:00 AM daily for 14 days. The animals were sacrificed at the end of Day 14, and blood samples were taken and analyzed for lipid and lipoprotein content. The results are presented in Table 3 below.

TABLE 3

Effects of Two Weeks of Treatment With CI-981, CI-1027, and Combination CI-981 + CI-1027 in LDL Receptor Knockout Mice

| Control | mg/kg/day | N | Triglycerides (mg/dL) | Total Cholesterol (mg/dL) | VLDL (mg/dL) | LDL (mg/dL) | HDL (mg/dL) | HDL VLDL + LDL |
|---|---|---|---|---|---|---|---|---|
|  |  | 10 | 79 ± 7 | 329 ± 23 | 6.3 ± 0.5 | 246 ± 20 | 76 ± 6 | 0.32 ± 0.03 |
| CI-981 | 60 | 10 | 86 ± 5 | 261 ± 23 | 11.8 ± 2.4 | 192 ± 24 | 57 ± 5 | 0.33 ± 0.04 |
| CI-1027 | 60 | 10 | 110 ± 20 | 208 ± 13 | 11.2 ± 4.0 | 110 ± 12 | 85 ± 11 | 0.84 ± 0.15 |
| CI-981 + CI-1027 | 30/30 | 10 | 88 ± 9 | 173 ± 10 | 8.1 ± 2.0 | 104 ± 9 | 62 ± 5 | 0.6 ± 0.08 |
| CI-981 + CI-1027 | 60/60 | 10 | 90 ± 7 | 139 ± 12 | 8.5 ± 2.7 | 70 ± 8 | 60 ± 3 | 0.83 ± 0.07 |

Table 4 below shows the percentage (%) change in the treatment group compared to the control group.

TABLE 4

Percentage Change From Controls Caused by CI-981, CI-1027, and CI-981 + CI-1027 in LDL Receptor Knockout Mice

| Control | mg/kg/day | N | Triglycerides (mg/dL) | Total Cholesterol (mg/dL) | VLDL (mg/dL) | LDL (mg/dL) | HDL (mg/dL) | HDL VLDL + LDL |
|---|---|---|---|---|---|---|---|---|
|  |  | 10 | 0 | 0 | 0 | 0 | 0 | 0 |
| CI-981 | 60 | 10 | 9 | −21 | 87 | −22 | −25 | 3 |
| CI-1027 | 60 | 10 | 39 | −37 | 78 | −55 | 12 | 162 |
| CI-981 + CI-1027 | 30/30 | 10 | 11 | −47 | 29 | −58 | −19 | 88 |
| CI-981 + CI-1027 | 60/60 | 10 | 14 | −58 | 35 | −72 | −21 | 159 |

The foregoing data from Examples 1 and 2 establish a dramatic and surprising metabolic effect achieved by combining a statin with a carboxyalkylether according to this invention.

Example 3

Effect of Compound of Formula III and a Statin, Alone and in Combination, on the Treatment of Atherosclerosis This study is a prospective randomized evaluation of the effect of a combination of the compound of Formula III (compound III) or a pharmaceutically acceptable salt thereof and a statin on the progression/regression of coronary and carotid artery disease. The study is used to show that a combination of the compound of Formula III or a pharmaceutically acceptable acid addition salt and a statin such as atorvastatin calcium is effective in slowing or arresting the progression or causing regression of existing coronary artery disease (CAD) as evidenced by changes in coronary angiography or carotid ultrasound, in subjects with established disease.

This study is an angiographic documentation of coronary artery disease carried out as a double-blind, placebo-controlled trial of a minimum of about 500 subjects and preferably of about 780 to about 1200 subjects. It is especially preferred to study about 1200 subjects in this study. Subjects are admitted into the study after satisfying certain entry criteria set forth below.

Entry criteria: Subjects accepted for entry into this trial must satisfy certain criteria. Thus, the subject must be an adult, either male or female, aged 18 to 80 years of age in whom coronary angiography is clinically indicated. Subjects will have angiographic presence of a significant focal lesion such as 30% to 50% on subsequent evaluation by quantitative coronary angiography (QCA) in a minimum of one segment (non-PTCA, non-bypassed, or non-MI vessel) that is judged not likely to require intervention over the next 3 years. It is required that the segments undergoing analysis have not been interfered with. Since percutaneous transluminal cardiac angioplasty (PTCA) interferes with segments by the insertion of a balloon catheter, non-PTCA segments are required for analysis. It is also required that the segments to be analyzed have not suffered a thrombotic event, such as a myocardial infarct (MI). Thus, the requirement for non-MI vessels. Segments that will be analyzed include: left main, proximal, mid and distal left anterior descending, first and second diagonal branch, proximal and distal left circumflex, first or largest space obtuse marginal, proximal, mid and distal right coronary artery. Subjects will have an ejection fraction of greater than 30% determined by catheterization or radionuclide ventriculography or ECHO cardiogram at the time of the qualifying angiogram or within the previous 3 months of the acceptance of the qualifying angiogram provided no intervening event such as a thrombotic event or procedure such as PTCA has occurred.

Generally, due to the number of patients and the physical limitations of any one facility, the study is carried out at multiple sites. At entry into the study, subjects undergo quantitative coronary angiography as well as B-mode carotid artery ultrasonography and assessment of carotid arterial compliance at designated testing centers. This establishes baselines for each subject. Once admitted into the test, subjects are randomized to receive the compound of Formula III (200 mg) and placebo or a statin (dose is dependent upon the particular statin used; however, generally 80 mg will be used at first) and placebo or compound III (200 mg) and a statin (80 mg). It will be recognized by a skilled person that the free base form or other salt forms of compound III or the free base form or other salt forms of the statin may be used in this invention. Calculation of the dosage amount for these other forms of the statin and compound III is easily accomplished by performing a simple ratio relative to the molecular weights of the species involved. The amount of compound III may be varied as required. Generally, a subject will start out taking 200 mg, and the amount will be titrated down to as little as 50 mg as determined by the clinical physician. The amount of the statin will similarly be titrated down from 80 mg if it is determined by the physician to be in the best interests of the subject. The subjects are monitored for a 1- to 3-year period, generally 3 years being preferred. B-mode carotid ultrasound assessment of carotid artery atherosclerosis and compliance are performed at regular intervals throughout the study.

Generally, 6-month intervals are suitable. Typically this assessment is performed using B-mode ultrasound equipment. However, a person skilled in the art may use other methods of performing this assessment. Coronary angiography is performed at the conclusion of the 1- to 3-year treatment period. The baseline and posttreatment angiograms and the intervening carotid artery B-mode ultrasonograms are evaluated for new lesions or progression of existing atherosclerotic lesions. Arterial compliance measurements are assessed for changes from baseline and over the 6-month evaluation periods.

The primary objective of this study is to show that the combination of carboxyalkylether or a pharmaceutically acceptable acid addition salt and a statin reduces the progression of atherosclerotic lesions as measured by quantitative coronary angiography (QCA) in subjects with clinical coronary artery disease. QCA measures the opening in the lumen of the arteries measured.

The primary endpoint of the study is the change in the average mean segment diameter of the coronary artery tree. Thus, the diameter of an arterial segment is measured at various portions along the length of that segment. The average diameter of that segment is then determined. After the average segment diameter of many segments has been determined, the average of all segment averages is determined to arrive at the average mean segment diameter. The mean segment diameter of subjects taking a statin and compound III or a pharmaceutically acceptable acid addition salt will decline more slowly, will be halted completely, or there will be an increase in the mean segment diameter. These results represent slowed progression of atherosclerosis, no change in the progression of atherosclerosis, and regression of atherosclerosis, respectively.

The secondary objective of this study is that the combination of carboxyalkylether or a pharmaceutically acceptable acid addition salt and a statin reduces the rate of progression of atherosclerosis in the carotid arteries as measured by the slope of the maximum intimal-medial thickness measurements averaged over 12 separate wall segments (Mean Max) as a function of time, more than does compound III or a pharmaceutically acceptable acid addition salt or a statin alone. The intimal-medial thickness of subjects taking a statin and compound III or a pharmaceutically acceptable salt thereof will increase more slowly, will cease to increase, or will decrease. These results represent slowed progression of atherosclerosis, halted progression of atherosclerosis, and regression of atherosclerosis, respectively. Further, these results may be used to facilitate dosage determinations.

The utility of the compounds of the present invention as medical agents in the treatment of angina pectoris in mammals (e.g., humans) is demonstrated by the activity of the compounds of this invention in conventional assays and the clinical protocol described below.

Example 4

Effect of Compound of Formula III and a Statin, Alone and in Combination, on the Treatment of Angina This study is a double-blind, parallel-arm, randomized study to show the effectiveness of compound III or a pharmaceutically acceptable acid addition salt thereof and a statin given in combination in the treatment of symptomatic angina.

Entry criteria: Subjects are males or females between 18 and 80 years of age with a history of typical chest pain associated with one of the following objective evidences of cardiac ischemia: (1) stress test segment elevation of about one millimeter or more from the ECG; (2) positive treadmill stress test; (3) new wall motion abnormality on ultrasound; or (4) coronary angiogram with a significant qualifying stenosis. Generally a stenosis of about 30% to 50% is considered to be significant.

Each subject is evaluated for about 10 to 32 weeks. At least 10 weeks are generally required to complete the study. Sufficient subjects are used in this screen to ensure that about 200 to 800 subjects and preferably about 400 subjects are evaluated to complete the study. Subjects are screened for compliance with the entry criteria, set forth below, during a 4-week run-in phase. After the screening criteria are met, subjects are washed out from their current anti-anginal medication and stabilized on a long acting nitrate such as nitroglycerine, isosorbide-5-mononitrate or isosorbide dinitrate. The term "washed out", when used in connection with this screen, means the withdrawal of current anti-anginal medication so that substantially all of said medication is eliminated from the body of the subject. A period of 8 weeks is preferably allowed for both the washout period and for the establishment of the subject on stable doses of said nitrate. Subjects having one or two attacks of angina per week while on stable doses of long acting nitrate are generally permitted to skip the washout phase. After subjects are stabilized on nitrates, the subjects enter the randomization phase provided the subjects continue to have either one or two angina attacks per week. In the randomization phase, the subjects are randomly placed into one of the four arms of the study set forth below. After completing the washout phase, subjects in compliance with the entry criteria undergo 24-hour ambulatory electrocardiogram (ECG) such as Holter monitoring, exercise stress testing such as a treadmill, and evaluation of myocardial perfusion using photon emission tomography (PET) scanning to establish a baseline for each subject. When conducting a stress test, the speed of the treadmill and the gradient of the treadmill can be controlled by a technician. The speed of the treadmill and the angle of the gradient are generally increased during the test. The time intervals between each speed and gradient increase is generally determined using a modified Bruce Protocol.

After the baseline investigations have been completed, subjects are initiated on one of the following four arms of the study: (1) placebo; (2) a statin (about 2.5 mg to about 160 mg); (3) compound III (about 25 mg to about 200 mg); or (4) a combination of the above doses of compound III and a statin together. The subjects are then monitored for 2 to 24 weeks. It will be recognized by a skilled person that the free base form or other salt forms of compound III or the free base form or other salt forms of the statin may be used in this invention. Calculation of the dosage amount for these other forms of the statin and compound III is easily accomplished by performing a simple ratio relative to the molecular weights of the species involved.

After the monitoring period has ended, subjects will undergo the following investigations: (1) 24-hour ambulatory ECG, such as Holter monitoring; (2) exercise stress testing (e.g., treadmill using said modified Bruce Protocol); and (3) evaluation of myocardial perfusion using PET scanning. Patients keep a diary of painful ischemic events and nitroglycerine consumption. It is generally desirable to have an accurate record of the number of anginal attacks suffered by the patient during the duration of the test. Since a patient generally takes nitroglycerin to ease the pain of an anginal attack, the number of times that the patient administers nitroglycerine provides a reasonably accurate record of the number of anginal attacks.

To demonstrate the effectiveness and dosage of the drug combination of this invention, the person conducting the test will evaluate the subject using the tests described. Successful treatment will yield fewer instances of ischemic events as detected by ECG, will allow the subject to exercise longer or at a higher intensity level on the treadmill or to exercise without pain on the treadmill, or will yield better perfusion or fewer perfusion defects on PET.

The utility of the compounds of the present invention as medical agents in the treatment of hypertension and hyperlipidemia in mammals (e.g., humans) suffering from a combination of hypertension and hyperlipidemia is demonstrated by the activity of the compounds of this invention in conventional assays and the clinical protocol described below.

Example 5

Effects of Carboxyalkylether and a Statin, Alone and in Combination, on the Treatment of Subjects Having Both Hypertension and Hyperlipidemia This study is a double-blind, parallel-arm, randomized study to show the effectiveness of carboxyalkylether or a pharmaceutically acceptable acid addition salt thereof and a statin given in combination in controlling both hypertension and hyperlipidemia in subjects who have mild, moderate, or severe hypertension and hyperlipidemia.

Each subject is evaluated for 10 to 20 weeks and preferably for 14 weeks. Sufficient subjects are used in this screen to ensure that about 400 to 800 subjects are evaluated to complete the study.

Entry criteria: Subjects are male or female adults between 18 and 80 years of age having both hyperlipidemia and hypertension. The presence of hyperlipidemia is evidenced by evaluation of the LDL cholesterol level of the subject relative to certain positive risk factors. If the subject has no coronary heart disease (CHD) and has less than two positive risk factors, then the subject is considered to have hyperlipidemia, which requires drug therapy if the LDL of the subject is ≥190 mg/dL. If the subject has no CHD and has two or more positive risk factors, then the subject is considered to have hyperlipidemia, which requires drug therapy if the LDL of the subject is ≥160 mg/dL. If the subject has CHD, then the subject is considered to have hyperlipidemia if the LDL of the subject is ≥130 mg/dL.

Positive risk factors include: (1) male over 45, (2) female over 55 wherein said female is not undergoing hormone replacement therapy (HRT), (3) family history of premature cardiovascular disease, (4) the subject is a current smoker, (5) the subject has diabetes, (6) an HDL of less than 45 mg/dL, and (7) the subject has hypertension. An HDL of >60 mg/dL is considered a negative risk factor and will offset one of the above mentioned positive risk factors.

The presence of hypertension is evidenced by a sitting diastolic blood pressure (BP) of >90 mmHg or sitting systolic BP of >140 mmHg. All blood pressures are generally determined as the average of three measurements taken 5 minutes apart.

Subjects are screened for compliance with the entry criteria set forth above. After all screening criteria are met, subjects are washed out from their current antihypertensive and lipid lowering medication and are placed on the NCEP ATP II Step 1 diet. The NCEP ATP II (adult treatment panel, 2nd revision) Step 1 diet sets forth the amount of saturated and unsaturated fat which can be consumed as a proportion of the total caloric intake. The term "washed out", where used in connection with this screen, means the withdrawal of current antihypertensive and lipid lowering medication so that substantially all of said medication is eliminated from the body of the subject. Newly diagnosed subjects generally remain untreated until the test begins. These subjects are also placed on the NCEP Step 1 diet. After the 4-week washout and diet stabilization period, subjects undergo the following baseline investigations: (1) blood pressure and (2) fasting lipid screen. The fasting lipid screen determines baseline lipid levels in the fasting state of a subject. Generally, the subject abstains from food for 12 hours, at which time lipid levels are measured.

After the baseline investigations are performed, subjects are started on one of the following: (1) a fixed dose of compound III, generally about 25 to 200 mg; (2) a fixed dose of a statin, generally about 2.5 mg to about 160 mg; or (3) a combination of the above doses of compound III and a statin together. It will be recognized by a skilled person that the free base form or other salt forms of compound III or the free base form or other salt forms of the statin may be used in this invention. Calculation of the dosage amount for these other forms of the statin and compound III is easily accomplished by performing a simple ratio relative to the molecular weights of the species involved. Subjects remain on these doses for a minimum of 6 weeks, and generally for no more than 8 weeks. The subjects return to the testing center at the conclusion of the 6 to 8 weeks so that the baseline evaluations can be repeated. The blood pressure of the subject at the conclusion of the study is compared with the blood pressure of the subject upon entry. The lipid screen measures the total cholesterol, LDL-cholesterol, HDL-cholesterol, triglycerides, apoB, very low-density lipoprotein (VLDL) and other components of the lipid profile of the subject. Improvements in the values obtained after treatment relative to pretreatment values indicate the utility of the drug combination.

The utility of the compounds of the present invention as medical agents in the management of cardiac risk in mammals (e.g., humans) at risk for an adverse cardiac event is demonstrated by the activity of the compounds of this invention in conventional assays and the clinical protocol described below.

Example 6

Effects of Carboxyalkylether and a Statin, Alone and in Combination, on Subjects at Risk of Future Cardiovascular Events This study is a double-blind, parallel-arm, randomized study to demonstrate the effectiveness of carboxyalkylether or a pharmaceutically acceptable acid addition salt and a statin given in combination in reducing the overall calculated risk of future events in subjects who are at risk for having future cardiovascular events. This risk is calculated by using the Framingham Risk Equation. A subject is considered to be at risk of having a future cardiovascular event if that subject is more than one standard deviation above the mean as calculated by the Framingham Risk Equation. The study is used to evaluate the efficacy of a fixed combination of carboxyalkylether or a pharmaceutically acceptable acid addition salt and a statin in controlling cardiovascular risk by controlling both hypertension and hyperlipidemia in patients who have both mild to moderate hypertension and hyperlipidemia.

Each subject is evaluated for 10 to 20 weeks and preferably for 14 weeks. Sufficient subjects are recruited to ensure that about 400 to 800 subjects are evaluated to complete the study.

Entry criteria: Subjects included in the study are male or female adult subjects between 18 and 80 years of age with a baseline 5-year risk, which risk is above the median for said subject's age and sex, as defined by the Framingham Heart Study, which is an ongoing prospective study of adult men and women showing that certain risk factors can be used to predict the development of coronary heart disease. The age, sex, systolic and diastolic blood pressure, smoking habit, presence or absence of carbohydrate intolerance, presence or absence of left ventricular hypertrophy, serum cholesterol, and HDL of more than one standard deviation above the norm for the Framingham Population are all evaluated in determining whether a patient is at risk for adverse cardiac event. The values for the risk factors are inserted into the Framingham Risk Equation and calculated to determine whether a subject is at risk for a future cardiovascular event.

Subjects are screened for compliance with the entry criteria set forth above. After all screening criteria are met, patients are washed out from their current antihypertensive and lipid lowering medication and any other medication which will impact the results of the screen. The patients are then placed on the NCEP ATP II Step 1 diet, as described above. Newly diagnosed subjects generally remain untreated until the test begins. These subjects are also placed on the NCEP ATP II Step 1 diet. After the 4-week washout and diet stabilization period, subjects undergo the following baseline investigations: (1) blood pressure; (2) fasting; (3) lipid screen; (4) glucose tolerance test; (5) ECG; and (6) cardiac ultrasound. These tests are carried out using standard procedures well-known to persons skilled in the art. The ECG and the cardiac ultrasound are generally used to measure the presence or absence of left ventricular hypertrophy.

After the baseline investigations are performed, patients will be started on one of the following: (1) a fixed dose of compound III (about 25 to 200 mg); (2) a fixed dose of a statin (about 2.5 mg to about 160 mg); or (3) the combination of the above doses of compound III and a statin. Patients are kept on these doses and are asked to return in 6 to 8 weeks so that the baseline evaluations can be repeated. At this time, the new values are entered into the Framingham Risk Equation to determine whether the subject has a lower, greater, or no change in the risk of future cardiovascular event.

The above assays demonstrating the effectiveness of compound III or pharmaceutically acceptable acid addition salts thereof and atorvastatin or pharmaceutically acceptable salts thereof in the treatment of angina pectoris, atherosclerosis, hypertension and hyperlipidemia together, and the management of cardiac risk, also provide a means whereby the activities of the compounds of this invention can be compared between themselves and with the activities of other known compounds. The results of these comparisons are useful for determining dosage levels in mammals, including humans, for the treatment of such diseases.

The following dosage amounts and other dosage amounts set forth elsewhere in this specification and in the appendant claims are for an average human subject having a weight of about 65 kg to about 70 g. The skilled practitioner will readily be able to determine the dosage amount required for a subject whose weight falls outside the 65 to 70 kg range, based upon the medical history of the subject and the presence of diseases, e.g., diabetes, in the subject. All doses set forth herein, and in the appendant claims, are daily doses.

In general, in accordance with this invention, the carboxyalkylether is generally administered in a dosage of about 25 mg to about 500 mg. Preferably, compound III is administered in a dosage of about 5 mg to about 100 mg. It will be recognized by a skilled person that the free base form or other salt forms of compound III may be used in this invention. Calculation of the dosage amount for these other forms of or the free base form or other salt forms of compound III is easily accomplished by performing a simple ratio relative to the molecular weights of the species involved.

In general, in accordance with this invention, the above statins are administered in the following dosage amounts:

Simvastatin, generally about 2.5 mg to about 160 mg and preferably about 10 mg to about 40 mg;

Pravastatin, generally about 2.5 mg to about 160 mg and preferably about 10 mg to about 40 mg;

Cerivastatin, generally about 25 µg to about 5 mg and preferably about 1 mg to about 3.2 mg;

Fluvastatin, generally about 2.5 mg to about 160 mg and preferably about 20 mg to about 80 mg;

Lovastatin, generally about 2.5 mg to about 160 mg and preferably about 10 mg to about 80 mg; and Atorvastatin, generally about 2.5 mg to about 160 mg and preferably about 10 mg to about 80 mg.

It will be recognized by a skilled person that the free base form or other salt forms of the above statins may be used in this invention. Calculation of the dosage amount for these other forms of or the free base form or other salt forms said statins is easily accomplished by performing a simple ratio relative to the molecular weights of the species involved.

The compounds of the present invention are generally administered in the form of a pharmaceutical composition comprising at least one of the compounds of this invention together with a pharmaceutically acceptable carrier or diluent. Thus, the compounds of this invention can be administered either individually or together in any conventional oral, parenteral, or transdermal dosage form.

For oral administration, a pharmaceutical composition can take the form of solutions, suspensions, tablets, pills, capsules, powders, and the like. Tablets containing various excipients such as sodium citrate, calcium carbonate, and calcium phosphate are employed along with various disintegrants such as starch and preferably potato or tapioca starch and certain complex silicates, together with binding agents such as polyvinylpyrrolidone, sucrose, gelatin, and acacia. Additionally, lubricating agents such as magnesium stearate, sodium lauryl sulfate, and talc are often very useful for tableting purposes. Solid compositions of a similar type are also employed as fillers in soft- and hard-filled gelatin capsules; preferred materials in this connection also include lactose or milk sugar, as well as high molecular weight polyethylene glycols. When aqueous suspensions and/or elixirs are desired for oral administration, the compounds of this invention can be combined with various sweetening agents, flavoring agents, coloring agents, emulsifying agents, and/or suspending agents, as well as such diluents as water, ethanol, propylene glycol, glycerin, and various like combinations thereof.

The combinations of this invention may also be administered in a controlled release formulation such as a slow release or a fast release formulation. Such controlled release formulations of the combination of this invention may be prepared using methods well-known to those skilled in the art. The method of administration will be determined by the attendant physician or other person skilled in the art after an evaluation of the subject's condition and requirements. The generally preferred formulation of atorvastatin calcium is Lipitor® as described in U.S. Pat. No. 5,686,104 incorporated herein by reference.

For purposes of parenteral administration. solutions in sesame or peanut oil or in aqueous propylene glycol can be employed, as well as sterile aqueous solutions of the corresponding water-soluble salts. Such aqueous solutions may be suitably buffered, if necessary, and the liquid diluent first rendered isotonic with sufficient saline or glucose. These aqueous solutions are especially suitable for intravenous, intramuscular, subcutaneous, and intraperitoneal injection purposes. In this connection, the sterile aqueous media employed are all readily obtainable by standard techniques well-known to those skilled in the art.

Methods of preparing various pharmaceutical compositions with a certain amount of active ingredient are known, or will be apparent in light of this disclosure, to those skilled in this art. For examples, see *Remington's Pharmaceutical Sciences*, Mack Publishing Company, Easter, Pa., 15th Edition (1975).

Pharmaceutical compositions according to the invention may contain 0.1% to 95% of the compound(s) of this invention, preferably 1% to 70%. In any event, the composition or formulation to be administered will contain a quantity of a compound(s) according to the invention in an amount effective to treat the condition or disease of the subject being treated.

Since the present invention relates to the treatment of diseases and conditions with a combination of active ingredients which may be administered separately, the invention also relates to combining separate pharmaceutical compositions in kit form. The kit includes two separate pharmaceutical compositions: a carboxyalkylether or a pharmaceutically acceptable acid addition salt thereof and a statin or a pharmaceutically acceptable salt thereof. The kit includes container means for containing the separate compositions such as a divided bottle or a divided foil packet; however, the separate compositions may also be contained within a single, undivided container. Typically, the kit includes directions for the administration of the separate components to achieve synergistic results. The kit form is particularly advantageous when the separate components are preferably administered in different dosage forms (e.g., oral and parenteral), are administered at different dosage intervals, or when titration of the individual components of the combination is desired by the prescribing physician.

It should be understood that the invention is not limited to the particular embodiments described herein, but that various changes and modifications may be made without departing from the spirit and scope of this novel concept as defined by the following claims.

What is claimed is:

1. A pharmaceutical composition comprising:
   a. 6,6'-oxybis(2,2-dimethylhexanoic acid) or a pharmaceutically acceptable acid addition salt thereof;
   b. an amount of a statin or a pharmaceutically acceptable salt thereof; and
   c. a pharmaceutically acceptable carrier or diluent.

2. The pharmaceutical composition of claim 1 wherein said statin is atorvastatin, simvastatin, pravastatin, rivastatin, mevastatin, fluindostatin, velostatin, fluvastatin, dalvastatin, dihydrocompactin, compactin, cerivastatin, or lovastatin; or a pharmaceutically acceptable salt thereof.

3. The pharmaceutical composition of claim 2 wherein said statin is atorvastatin, simvastatin, pravastatin, mevastatin, lovastatin, cerivastatin, or a pharmaceutically acceptable salt thereof.

4. The pharmaceutical composition of claim 1, wherein the statin is atorvastatin or a pharmaceutically acceptable addition salt thereof.

5. A method of treating a condition wherein the condition is hyperlipidemia, angina pectoris, atherosclerosis, or is a condition characterized by the presence of both hypertension and hyperlipidemia comprising
   (a) administering to a patient in need thereof an effective amount of 6,6'-oxybis(2,2-dimethylhexanoic acid) or a pharmaceutically acceptable acid addition salt thereof; and
   (b) administering to the patient an amount of a statin or a pharmaceutically acceptable salt thereof.

6. The method of claim 5 wherein said statin is atorvastatin, simvastatin, pravastatin, rivastatin, mevastatin, fluindostatin, velostatin, fluvastatin, dalvastatin, dihydrocompactin, compactin, cerivastatin, or lovastatin; or a pharmaceutically acceptable salt thereof.

7. The method of claim 6 wherein said statin is atorvastatin, simvastatin, pravastatin, mevastatin, lovastatin, cerivastatin, or a pharmaceutically acceptable salt thereof.

8. The method of claim 7 wherein the statin is atorvastatin calcium.

9. The method of claim 5 wherein the condition is hyperlipidemia.

10. The method of claim 5 wherein the condition is atherosclerosis.

11. The method of claim 10 wherein the method of treating slows the progression of atherosclerotic plaques.

* * * * *

UNITED STATES PATENT AND TRADEMARK OFFICE
CERTIFICATE OF CORRECTION

| | | |
|---|---|---|
| PATENT NO. | : 8,557,835 B2 | Page 1 of 1 |
| APPLICATION NO. | : 11/961032 | |
| DATED | : October 15, 2013 | |
| INVENTOR(S) | : Bisgaier et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 958 days.

Signed and Sealed this
Twenty-first Day of April, 2015

Michelle K. Lee
*Director of the United States Patent and Trademark Office*